US005162207A

United States Patent [19]

Nagarajan et al.

[11] Patent Number: 5,162,207

[45] Date of Patent: Nov. 10, 1992

[54] **SUCROSE INDUCIBLE EXPRESSION VECTORS FOR *BACILLUS* SP.**

[75] Inventors: Vasantha Nagarajan; Leslie B. Tang, both of Wilmington, Del.

[73] Assignee: E. I. Du Pont de Nemours and Company, Wilmington, Del.

[21] Appl. No.: 376,474

[22] Filed: Jul. 7, 1989

[51] Int. Cl.[5] ...................... C12N 15/11; C12N 15/63; C12N 15/67

[52] U.S. Cl. ................................ 435/69.1; 435/252.3; 435/320.1; 536/27

[58] Field of Search ................... 435/69.7, 172.3, 69.1, 435/43; 536/27

[56] References Cited

U.S. PATENT DOCUMENTS 4,769,327 9/1988 Stephens et al. ............ 435/172.3 X
4,801,537 1/1989 Nagarajan .................... 435/172.3 X
4,917,999 4/1990 Byng et al. ............................ 435/6

FOREIGN PATENT DOCUMENTS 2091268 12/1984 United Kingdom .

OTHER PUBLICATIONS

FEMS Micro. Letts. 52:117-120, Jul. 1988, Edelman et al. A system for the inducible secretion of proteins from *Bacillus subtilis* during logarithmic growth.

Gene 24:255-263, 1983, Yoshimura et al. Construction of a *Bacillus subtilis* cloning vehicle with heterologous DNA sequence.

Palva et al., Proc. Natl. Acad. Sci. U.S.A. 79, 5582-5586 (1982).

Palva et al., Gene, 22, 229-235 (1983).

Vasantha et al., J. Bacteriol., 165, 837-842.

Honjo et al., J. Biotech 4, 63-71 (1986).

Joyet et al., Bacillus: Molecular Genetics and Biotechnology Applications, eds. Ganesan & Hoch (Academic Press, 1986), 479-493.

Lepesant et al., in Microbiology, American Society of Microbiology (1976).

Debarbouille et al., FEMS Microbiol. Lett. 41, 137-140 (1987).

Shimotsu et al., J. Bacteriol. 168, 380-388 (1986).

Mantsala, P. and M. Puntab, FEMS Microbiol. Lett. 13, 395-399 (1982).

Steinmetz et al., Mol. Gen. Genet 200:200-228 (1985).

Sibakov, M. Eur. J. Biochem. 155, 572-581 (1986).

K. Ohmura et al., Nucleic Acids Research, vol. 12, No. 13, pp. 5307-5317 (1984).

*Primary Examiner*—David L. Lacey
*Assistant Examiner*—John D. Ulm

[57] ABSTRACT

A regulatable replicable recombinant expression vector comprises an expression element which is substantially homologous to a sucrose-regulatable expression element derived from a first *Bacillus* species, the vector, when containing a DNA sequence encoding a polypeptide to which the expression element is operably linked, being regulatable by sucrose and replicable when transformed into at least one *Bacillus* species different from the first *Bacillus* species.

18 Claims, 11 Drawing Sheets

FIG. 3a

```
GAATTCCTTCAGGAAAAGAACGATGGCTGTCTTATTAGCGGTTGCAGGCACATTTATTTTGGTCACACACGGGAATGTCGGCA
GCCTGTCTATATCCGGTCTGGCTGTTTTTTGGGGCATCAGCTCGGCATTTGCGCTGGCGTTTTACACCCTCCAGCCGCATCGGCT
TTTGAAGAAATGGGGCTCCGCCATTATTGTCGGATGGGGCATGCTGATGCGGAGCCGTTCTCAGCCTGATTCAGCCGCCTTGG
AAGTTTGAAGGCCAATGGTCGTTGTCCGCATATGCCGCGATCGTGTTTATCATCATTTTCGGAACGCTCATCGCTTTTTATT
GCTATTTGGAAAGCCTGAAATATCTGAGTGCCTCTGAAACCAGCCTCCTCGCCTGTGCAGAGCCGCTGTCAGCAGCTTTTTT
AGCGGTGATCTGGCTGCATGTTCCCTTCGGAATATCAGAATGGCTGGGTACTTTACTGATTTTAGCCACCATCGCTTTATT
ATCTATCAAGAAAAAATAACCTCTCTTTTTTAGAGAGGTTTTTCCCTAGGCCTGAAGCACCCTTTAGTCTCAATTACCCA
TAAATTAAAAGGCCTTTTTTCGTTTTACTATCATTCAAAAGAGGAAAATAGACCAGTTGTCAATAGAATCAGAGTCTAAT
AGAATGAGGTCGAAAAGTAAATCACGCAGGATTGTTACTGATAAAGCAGGCAAGACCTAAAATGTGTTAAGGGCAAAGTG
TATTCTTTGGCGTCATCCCTTACATATTTTGGGTCTTTTTTTCTGTAACAAACCTGCCATCCATGAATTCGGGAGGATCGAA
ACGGCAGATCGCAAAAAACAGTACATACAGAAGGAGACATGAAC

ATG AAC ATC AAA AAA ATT GTA AAA CAA GCC ACA GTT CTG
met asn ile lys lys ile val lys gln ala thr val leu
-29

ACT TTT ACG ACT GCA CTT CTG GCA GGA GGA GCG ACT CAA GCC TTC GCG | AAA GAA AAT AAC
thr phe thr thr ala leu leu ala gly gly ala thr gln ala phe ala | lys glu asn asn
                                                            -1    +1

CAA AAA GCA TAC AAA GAA ACG TAC GGC GTC TCT CAT ATT ACA CGC CAT GAT ATG CTG CAG
gln lys ala tyr lys glu thr tyr gly val ser his ile thr arg his asp met leu gln

ATC CCT AAA CAG CAG CAA AAC GAA AAA TAC CAA GTG CCT CAA TTC GAT CAA TCA ACG ATT
ile pro lys gln gln gln asn glu lys tyr gln val pro gln phe asp gln ser thr ile

AAA AAT ATT GAG TCT GCA AAA GGA CTT GAT GTG TGG GAC AGC TGG CCG CTG CAA AAC GCT
lys asn ile glu ser ala lys gly leu asp val trp asp ser trp pro leu gln asn ala
                    50

GAC GGA ACA GTA GCT GAA TAC AAC GGC TAT CAC GTT GTG TTT GCT CTT GCG GGA AGC CCG
asp gly thr val ala glu tyr asn gly tyr his val val phe ala leu ala gly ser pro
```

FIG.3a'

AAA GAC GCT GAT GAC ACA TCA ATC TAC ATG TTT TAT CAA AAG GTC GGC GAC AAC TCA ATC
lys asp ala asp asp thr ser ile tyr met phe tyr gln lys val gly asp asn ser ile
100

GAC AGC TGG AAA AAC GCG GGC CGT GTC TTT AAA GAC AGC GAT AAG TTC GAC GCC AAC GAT
asp ser trp lys asn ala gly arg val phe lys asp ser asp lys phe asp ala asn asp CCG ATC CTG AAA GAT CAG ACG CAA GAA TGG TCC GGT TCT GCA ACC TTT ACA TCT GAC GGA
pro ile leu lys asp gln thr gln glu trp ser gly ser ala thr phe thr ser asp gly AAA ATC CGT TTA TTC TAC ACT GAC TAT TCC GGT AAA CAT TAC GGC AAA CAA AGC CTG ACA
lys ile arg leu phe tyr thr asp tyr ser gly lys his tyr gly lys gln ser leu thr
150

ACA GCG CAG GTA AAT GTG TCA AAA TCT GAT GAC ACA CTC AAA ATC AAC GGA GTG GAA GAT
thr ala gln val asn val ser lys ser asp asp thr leu lys ile asn gly val glu asp CAC AAA ACG ATT TTT GAC GGA GAC GGA AAA ACA TAT CAG AAC GTT CAG CAG TTT ATC GAT
his lys thr ile phe asp gly asp gly lys thr tyr gln asn val gln gln phe ile asp
200

GAA GGC AAT TAT ACA TCC GGC GAC AAC CAT ACG CTG AGA GAC CCT CAC TAC GTT GAA GAC
glu gly asn tyr thr ser gly asp asn his thr leu arg asp pro his tyr val glu asp AAA GGC CAT AAA TAC CTT GTA TTC GAA GCC AAC ACG GGA ACA GAA AAC GGA TAC CAA GGC
lys gly his lys tyr leu val phe glu ala asn thr gly thr glu asn gly tyr gln gly GAA GAA TCT TTA TTT AAC AAA GCG TAC TAC GGC GGC GGC ACG AAC TTC TTC CGT AAA GAA
glu glu ser leu phe asn lys ala tyr tyr gly gly gly thr asn phe phe arg lys glu
250

AGC CAG AAG CTT CAG CAG AGC GCT AAA AAA CGC GAT GCT GAG TTA GCG AAC GGC GCC CTC
ser gln lys leu gln gln ser ala lys lys arg asp ala glu leu ala asn gly ala leu

FIG.3a''

GGT ATC ATA GAG TTA AAT AAT GAT TAC ACA TTG AAA AAA GTA ATG AAG CCG CTG ATC ACT
gly ile ile glu leu asn asn asp tyr thr leu lys lys val met lys pro leu ile thr
300

TCA AAC ACG GTA ACT GAT GAA ATC GAG CGC GCG AAT GTT TTC AAA ATG AAC GGC AAA TGG
ser asn thr val thr asp glu ile glu arg ala asn val phe lys met asn gly lys trp TAC TTG TTC ACT GAT TCA CGC GGT TCA AAA ATG ACG ATC GAT GGT ATT AAC TCA AAC GAT
tyr leu phe thr asp ser arg gly ser lys met thr ile asp gly ile asn ser asn asp ATT TAC ATG CTT GGT TAT GTA TCA AAC TCT TTA ACC GGC CCT TAC AAG CCG CTG AAC AAA
ile tyr met leu gly tyr val ser asn ser leu thr gly pro tyr lys pro leu asn lys ACA GGG CTT GTG CTG CAA ATG GGT CTT GAT CCA AAC GAT GTG ACA TTC ACT TAC TCT CAC
thr gly leu val leu gln met gly leu asp pro asn asp val thr phe thr tyr ser his TTC GCA GTG CCG CAA GCC AAA GGC AAC AAT GTG GTT ATC ACA AGC TAC ATG ACA AAC AGA
phe ala val pro gln ala lys gly asn asn val val ile thr ser tyr met thr asn arg
400

GGC TTC TTC GAG GAT AAA AAG GCA ACA TTT GGC CCA AGC TTC TTA ATG AAC ATC AAA GGC
gly phe phe glu asp lys lys ala thr phe gly pro ser phe leu met asn ile lys gly AAT AAA ACA TCC GTT GTC AAA AAC AGC ATC CTG GAG CAA GGA CAG CTG ACA GTC AAC TAA
asn lys thr ser val val lys asn ser ile leu glu gln gly gln leu thr val asn ***
443

TAACAGCAAAAAGAAAATGCCGATACTTCATTGGCATTTTCTTTTATTTCTCAACAAGATGGTGAATTC
2350

PUTATIVE PROMOTER

PUTATIVE REGULATORY REGION

SIGNAL PEPTIDE CODING REGION

LEVANSUCRASE CODING REGION

TRANSCRIPTION TERMINATOR

FIG.4 sacR37 [Bsu]

```
 10        20       30
C         A  CAA    AUAC
AAGA CUAAAAUGUGUAA GGG  AGUGU    U
UUCU GAUUUUAUACAUU CCC  UCACG    U
    (A)          -    ---   CGGU
 60       50              40
```

Energy:-20.1 sacB [BamP]

```
 10            20      30
            U  CAAA    AUU
AAGACCUAAAAUGUGU AAGGG  GUGU    C
UUCUGGUUUUAUACA UUCCC  UGCG    U
                -   -UAC   GUU
 60            50          40
```

Energy:-24.5 sacB [Bsu]

```
 10        20       30
          A  CAA    AUAC
AAGACCUAAAAUGUGUAA GGG  AGUGU    U
UUCUGGAUUUUAUACAUU CCC  UCACG    U
                 -   ---    CGGU
 60       50              40
```

Energy:-25.9 sacR36 [Bsu]

```
 10        20       30
          A  CAAA(A)  AUAC
AAGACCUAAAAUGUGUAA GGG  UGU    U
UUCUGGAUUUUAUACAUU CCC  ACG    U
                 -   ---UC  CGGU
 60       50              40
```

Energy:-26.1

FIG. 6

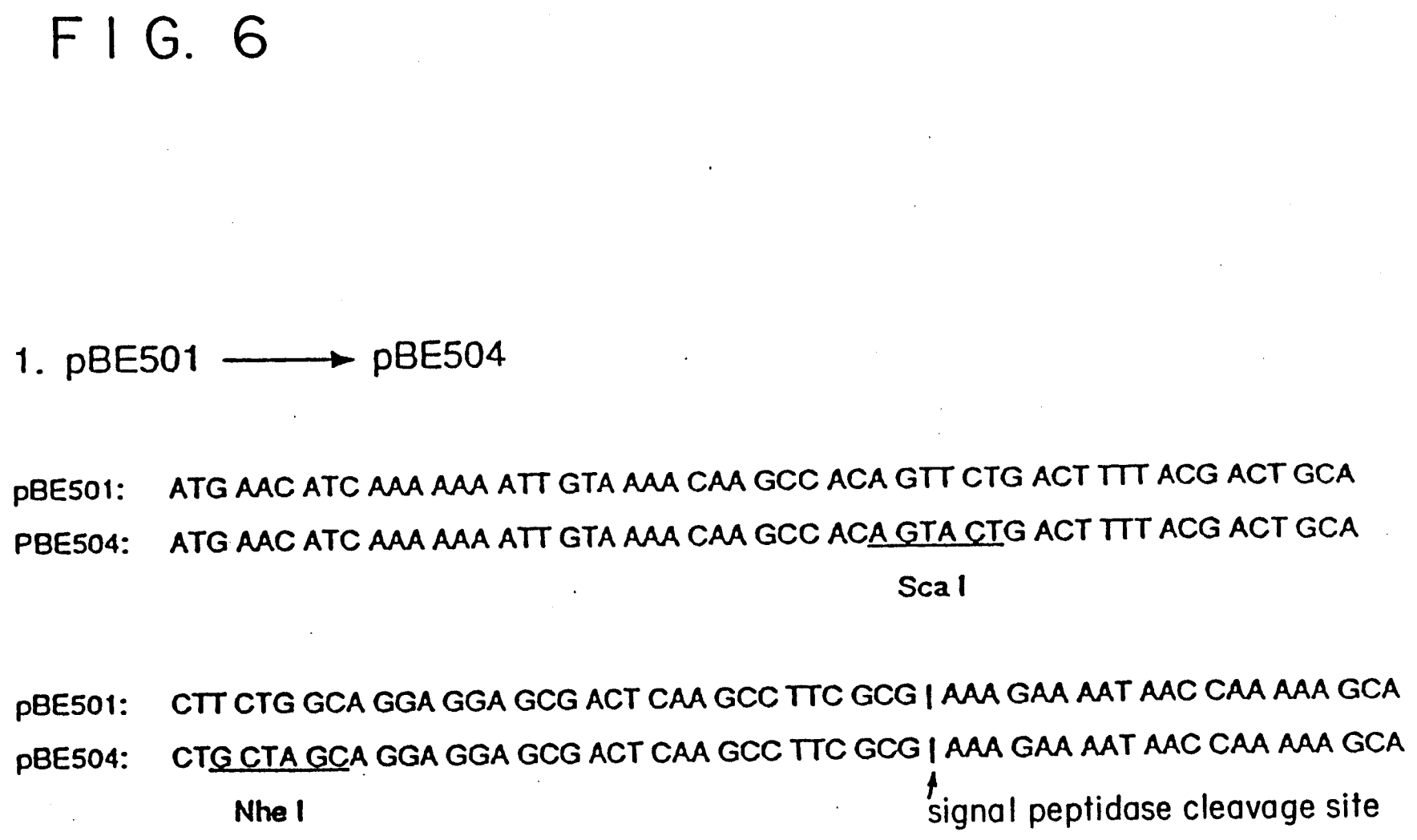

1. pBE501 ⟶ pBE504 pBE501: ATG AAC ATC AAA AAA ATT GTA AAA CAA GCC ACA GTT CTG ACT TTT ACG ACT GCA

PBE504: ATG AAC ATC AAA AAA ATT GTA AAA CAA GCC ACA GTA CTG ACT TTT ACG ACT GCA

Sca I pBE501: CTT CTG GCA GGA GGA GCG ACT CAA GCC TTC GCG | AAA GAA AAT AAC CAA AAA GCA pBE504: CTG CTA GCA GGA GGA GCG ACT CAA GCC TTC GCG | AAA GAA AAT AAC CAA AAA GCA

Nhe I

↑ signal peptidase cleavage site

FIG. 6'

2. pBE504 ⟶ pBE311 signal peptidase cleavage site

```
pBE504:  GCC  TTC  GCG| AAA  GAA  AAT  AAC  CAA  AAA  GCA
         ala  phe  ala  lys  glu  asn  asn  gln  lys  ala

                                 Eco RV
pBE311:  GCC  TTC  GCG| AAA  GAA  GÀT  ATC  AAT  AAC  CAA
         ala  phe  ala  lys  glu  asp  ile  asn  asn  glu
```

SUCROSE INDUCIBLE EXPRESSION VECTORS FOR *BACILLUS* SP.

BACKGROUND OF THE INVENTION

This invention relates to a regulatable and replicable expression and secretion vector useful for *B. subtilis* and other gram-positive bacteria.

Several expression and secretion vectors for heterologous protein production in *Bacillus subtilis* have been reported. These include α-amylase [Palva et al., Proc. Natl. Acad. Sci. USA 79:5582–5586 (1982); Palva et al., Gene, 22:229–235 (1983), and GB 2,091,268B] and protease gene-based vectors [Vasantha et al., J. Bacteriol., 165:837–842, (1986), Honjo et al., J. Biotech 4:63–71 (1986), and Nagarajan et al., U.S. Pat. No. 4,801,537]. A disadvantage of these vectors is that their expression is not regulated, and the heterologous protein is produced at all times. A *B. subtilis* secretion vector based on the levansucrase gene from *B. subtilis* (sacB[Bsu]) has also been reported by Joyet et al., in *Bacillus: Molecular Genetics and Biotechnology Applications,* eds. Ganesan & Hoch (Academic Press, 1986), 479–493. Edelman et al., FEMS Microbiology Letters 52:117–120 (1988) discloses such a vector which is replicable. However, the levansucrase gene on a multicopy plasmid vector is homologous to the chromosomal sacB[Bsu] gene of *B. subtilis bacteria;* therefore, extensive recombination may occur and result in plasmid instability. Thus there is a need for a stable, regulatable expression vector for cloning heterologous genes into *B. subtilis* and other gram positive bacteria which can overcome these disadvantages.

The *Bacillus subtilis* levansucrase expression system has several advantages as the basis for designing a regulatable expression system. It is regulatable by sucrose, which is inexpensive and easily purified from the protein product. However, a major obstacle which exists for genetic engineering of the levansucrase expression system is its complexity. There are at least two other genes present in the levansucrase regulon, sacS and sacU (Lepesant et al., in *Microbiology,* American Society of Microbiology [1976]; Debarbouille et al., FEMS Microbiol. Lett. 41, 137–140 [1987]), which are involved with the control of expression of the gene. The structural gene is transcriptionally regulated in a way or ways which are not well understood, but which may be related to the formation of particular structures in the regulatory region of the gene between the transcription initiation sequence and the translation start sequence. These structures may be destabilized by the very precise and delicate interactions between the products of the sacS and sacU genes in the presence of sucrose, thus causing antitermination and readthrough into the structural gene (Shimotsu et al., J. Bacteriol. 168:380–388 [1986]). Thus any attempts at genetically engineering the levansucrase expression system are complicated by the need to take into account compatibility with this complex regulon.

The mechanism of sucrose regulation of sacB[Bsu] has been studied by Shimotsu et al., suora. The DNA sequence of the regulatory region between the promoter and start site of translation consists of inverted repeats. Thus, the RNA structure has the potential to form a long stem and a short loop structure. Shimotsu et al. also determined the DNA sequence of two *B. subtilis* mutants that were no longer regulated by sucrose (levansucrase was expressed independently of sucrose). The mutations in both cases were found to be single-base changes in the regulatory region (see FIG. 4). Thus there was some indication that the regulation of levansucrase is very tightly controlled by the specific DNA sequence of this regulatory region in *B. subtilis.*

It is also known that at least one other species of Bacillus, e.g. *Bacillus amyloliquefaciens,* made a levansucrase (Mantsala, P. and M. Puntab, FEMS Microbiol. Lett. 13, 395–399 [1982]), but it was not known whether it was regulated in *B. amyloliquefaciens,* or, if so, whether the expression elements of the *B. amyloliquefaciens* gene would be compatible with the other genes of the *B. subtilis* sucrose regulon.

SUMMARY OF THE INVENTION

Therefore, in one aspect, this invention provides a regulatable replicable expression vector useful for expressing foreign proteins or polypeptides in gram positive host organisms, preferably *B. subtilis,* comprising the expression elements (promoter and regulatory sequences) from the levansucrase gene of *B. amyloliquefaciens,* wherein the promoter sequence controls the binding of RNA polymerase and the regulatory sequence regulates transcription by allowing transcription to occur only when sucrose is present, and a sequence encoding a protein or polypeptide linked operably to said expression elements. A preferred aspect is a regulatable replicable expression vector useful for expressing foreign proteins or polypeptides in gram positive organisms, preferably *B. subtilis,* comprising the expression elements from the levansucrase gene of *B. amyloliquefaciens,* a DNA sequence, from, for example, *B. amyloliquefaciens,* encoding a signal peptide, said sequence being located downstream from the regulatory sequence and a restriction endonuclease cleavage site, said site being located adjacent to and downstream from the signal sequence. The restriction endonuclease cleavage sites enable heterologous DNA sequences encoding foreign proteins or polypeptides to be easily placed adjacent to and in the proper reading frame with the signal sequence by conventional techniques. Gram positive bacteria, preferably *Bacillus,* preferably *B. subtilis* transformed with the preferred vector of this invention, can produce and secrete desired proteins or polypeptides.

Another preferred aspect of this invention provides a DNA fragment from the levansucrase gene from *B. amyloliquefaciens* (sacB[BamP] which permits the construction of a stable, regulatable expression vector that can be maintained on a multicopy plasmid. When transformed into *B. subtilis,* the vector on a multicopy plasmid is regulatable by sucrose. Even though the sacB-[BamP1 gene has homology with the sacB[Bsu1 gene, the homology is not sufficient for the sacB[BamP] to recombine with the chromosomal sacB[Bsu] locus. Thus, the vector of this invention can be used to produce a variety of heterologous polypeptides, either intracellularly or extracellularly in a stable and regulated manner.

Yet another aspect of this invention is to provide a method of regulatably expressing a heterologous polypeptide in gram positive bacteria comprising isolating a fragment of DNA containing the expression elements from the *B. amyloliquefaciens* gene encoding the enzyme levansucrase, modifying said fragment of DNA to contain an appropriately placed restriction endonuclease recognition site, adding said fragment to plasmids capable of existing and replicating in gram positive bacteria, especially *B. subtilis*, and thereby producing a vector which, in the presence of sucrose, causes gram positive bacteria transformed with it to intracellularly produce and/or secrete into the surrounding medium proteins whose genetic information is operably linked to said fragment in the vector.

It is another aspect of this invention to provide a method of expressing heterologous polypeptides in a constitutive, unregulated fashion by transforming a vector according to this invention into a host organism which does not have regulatory elements which are compatible with those of the vector.

BRIEF DESCRIPTION OF THE DRAWINGS

Various other objects, features, and attendant advantages of the present invention will become more fully appreciated as the same becomes better understood when considered in conjunction with the accompanying drawings and wherein:

FIG. 1 (bottom): Restriction map of *B. amyloliquefaciens* DNA. The letters denote restriction enzyme recognition sites as follows: E=EcoRI, RV==EcoRV, B=BamHI, P=Pstl, S=Sall, X=Xball, M=Smal, H=HindIII, K=Kpn.

FIGS. 3*a*, 3*a'* and 3*a''*: Collectively, the nucleotide sequence of the isolated sacB[BamP] fragment. Codon -29 is the start site of translation. +1 denotes the N-terminal amino acid of the mature levansucrase. The underlined portion denotes the putative regulatory sequence.

FIG. 4: Sequences and structures of proposed regulatory regions of sacB[Bsu], sacB[BamP], sacR36[Bsu] DNA sequence of 708–733 in FIG. 3 and *B. subtilis* DNA sequence 305–370 (Steinmetz et al., infra) have been analyzed and compared using Fold program in the Wisconsin.

FIG. 6: Construction of pBE311. pBE504 was constructed by site-directed mutagenesis from pBE501. II was constructed from pBE504. The signal peptide coding sequence of pBE501 and 504 are depicted, and the DNA sequence of the signal peptide coding region of pBE501 was independently determined and is the same as that of pBE301.

DEFINITIONS

Figure 1:
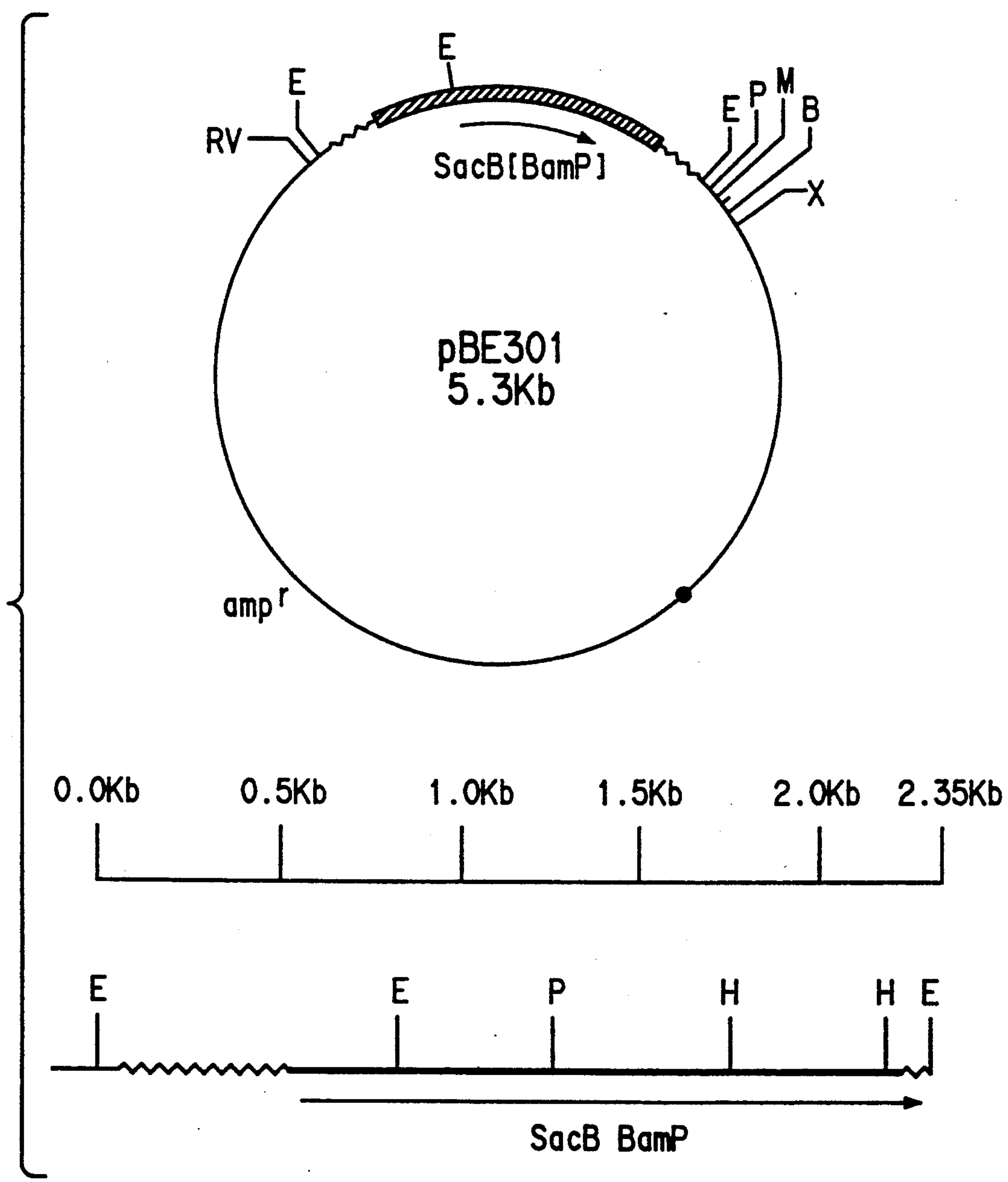
FIG. 1 (top): Plasmid map of pBE301, ▬ denotes sacB[BamP], MM denotes B. amyloliquefaciens DNA, ——denotes Blue Script vector DNA, and ∘ denotes the pBR322 origin of replication.

The following are definitions used herein:

| | |
|---|---|
| sacB[BamP]: | levansucrase gene from *B. amyloliquefaciens* |
| sacB[Bsu]: | levansucrase gene from *B. subtilis* |
| expression element: | promoter and regulatory nucleotide sequences |

-continued

| | |
|---|---|
| regulatory sequence: | sequence upstream of the start site of translation consisting of an inverted repeat sequence separated by a short distance and capable of forming a stem and loop structure |
| promoter sequence: | a sequence of nucleotide bases upstream of the start site of transcription and which is the site of binding of RNA polymerase |
| signal peptide: | amino terminal polypeptide preceding the secreted protein which is cleaved and not present in the mature protein, which has the function of directing and translocating the protein across the cell membrane |
| mature protein: | the final protein product (i.e., without signal peptide) |
| upstream sequences: | sequences proceeding in the opposite direction from expression |
| downstream sequences: | sequences proceeding in the direction of expression |
| sucrose: | includes sucrose, thiosucrose, related disaccharides and carbohydrates, and analogs thereof which will activate the regulatory sequence included in the vector |
| heterologous DNA sequences: | DNA sequences from any organism other than the bacteria containing the vector of this invention |
| foreign proteins: | proteins not normally produced by the bacterium containing the vector of this invention |
| recombination: | process by which DNA sequences located, for example, on a plasmid are exchanged with homologous sequences located, for example, on the chromosome |
| cm: | chloramphenicol |
| Kan: | kanamycin |
| Phagemids: | plasmids containing an M13 origin of replication |

The terms "proteins" and "polypeptides" are used interchangeably.

Standard microbiological methods well known to those in the art can be used for the growth and maintenance of bacterial cultures. Suitable methods of genetic engineering are described in Maniatis et al., *Molecular Cloning: A Laboratory Manual* (Cold Spring Harbor, New York: Cold Spring Harbor Laboratory, 1982), and in the instructions accompanying commercially available kits for genetic engineering. Bacterial cultures and plasmids necessary to carry out this invention are commercially available and, along with their sources, are identified in the text which follows.

Suitable amounts of inducing compounds, e.g., sucrose and its analogs, are routinely determinable by one of ordinary skill in the art.

Suitable host bacteria for the vectors of this invention are generally those which are gram positive, and particularly those belonging to the genus Bacillus. Non-limiting examples of such suitable host bacteria include *B. brevis, B. lichenformis*, and species of the genus *Streptomyces*. In addition, other bacteria, such as species whose regulatory elements are not compatible with those of the vector of this invention, including non-gram positive species such as, for example, *E. coli*, may be suitable hosts, for example, temporarily for further cloning or when regulation of the expression of the polypeptide is not desired. The regulation of expression may not be functional to the same degree in such other bacteria as it is when the vector is transformed into a gram positive bacteria such as *Bacillus*. In addition, the vectors of this invention may be transformed into host bacteria of which naturally produce the polypeptide which is carried on the vector. Preferably, the host bacterial strain has the chromosomal gene coding for the polypeptide deleted or mutated such that recombination cannot occur between the vector and the chromosomal gene, i.e., such that the vector is stable.

In the context of this invention, a preferred stable vector, for example, can be defined as one which, when transformed into a host organism in multiple, for example, greater than ten, copies, will not lose more than half of those copies after ten generations, especially as a result of recombination. It is a surprising aspect of this invention that a vector of this invention will generally be replicable as a multicopy plasmid without significant recombination or integration with the chromosomal DNA, in contrast with similar vectors in the prior art. However, it is also possible to employ the vector of this invention in bacteria where the expression system of this invention becomes integrated chromosomally.

Suitable vectors will generally be those which are compatible with the organism into which the vector will be transformed. Thus, for example, they will have compatible regulatory sequences and origins of replication, will be preferably multicopy and have a selectable marker gene, for example, a gene coding for antibiotic resistance. These can include phage, plasmid, cosmid and chromosomal integration vectors. In addition, the expression vector of this invention may be used to integrate the expression elements and heterologous gene sequences into the host chromosome by conventional techniques (Saunders et al., J. Bacteriol. 157, 718-726 [1984]). Without intending any limitations, examples of plasmids suitable to receive the fragment containing the expression element and other associated sequences include those with ATCC Accession Nos. 39294, 37278, 37277, 37105, 37280, and 37108. When transformed with a plasmid of this invention, gram-positive bacteria, especially *B. subtilis,* make levansucrase only when sucrose is present. Thus, for example, a vector of this invention can exist as an autonomous plasmid, both in *Escherichia coli* and *B. subtilis,* and expression of the heterologous protein is regulated by the presence or absence of sucrose in *B. subtilis.* The vector can be engineered to have a unique restriction endonuclease cleavage site for the easy insertion of DNA sequences encoding foreign proteins and polypeptides. *B. subtilis* transformed with the vector in which a sequence encoding a foreign protein has been appropriately placed, and which also contains an appropriate DNA sequence coding for a signal peptide, secretes said foreign protein into the medium when the bacteria are in the presence of sucrose.

Suitable inserted restriction endonuclease sites are those which are, preferably, unique for the rest of the vector and which code for amino acid sequences which do not adversely affect the function of the encoded protein or the regulatory or signal peptide sequences. In addition, the restriction sites can be blunt-ended sites which can be used to create other restriction sites by use of other linker sequences using known techniques (Maniatis, supra).

Suitable signal peptides can be derived from the same gene as the expression element or different, may be derived from the same gene as the heterologous polypeptide coding sequence or different, or may be modified or synthetic sequences tailored by known techniques to best suit the host and the polypeptide to be excreted. For example, difficulties in achieving secretion may be addressed by substituting a signal peptide having more or less hydrophobic amino acids, either in the core or at the ends of the sequence, making the signal peptide longer or shorter, or adding or removing charged residues, according to known methods. Preferred signal peptides can be isolated using known techniques (Smith et al., Gene 70, 351-361 [1988]) and are derived from, for example, *B. amyloliquefaciens* amylase, alkaline protease, or neutral protease.

Suitable polypeptides may be any polypeptides which are compatible with the host organism. They may be, for example, of viral, bacterial, fungal, plant, insect, or vertebrate, including mammalian origin. They may be, for example, structural proteins, enzymes, or peptides. Non-limiting examples include wheat o-amylase, HIV protease, elastin and immunoglobulins.

As is well known, the polypeptides produced by the method of this invention may be identical to the polypeptides produced by the organism from which the sequence was derived, or may be one or more amino acids longer or shorter than the native protein, or may be altered in any other way. This may be, for example, to provide the linkage between the expression element or the signal peptide and the polypeptide coding sequence, or to modify the polypeptide for other purposes. Methods for making these modifications are conventional (e.g., Maniatis et al., supra and Smith, M., Ann. Rev. Genet. 19, 423-462 [1985]). For example, the secretion vector constructed in Example 4 of this invention was made by cloning into the DNA sequence coding for the N-terminus of levansucrase a six base insertion coding for an adventitious restriction site; the resultant levansucrase contains an additional two amino acids coded for by this insertion, aspartic acid and isoleucine, which do not affect the activity of the levansucrase.

In the context of this invention, "operably linked" means that the synthesis and expression and/or secretion of the heterologouspolypeptide is regulated by the levansucrase expression element. Thus the hetrologous gene fusion can be either a transcriptional or a translational gene fusion.

In the context of this invention, "substantially homologous" means that the expression element may be derived from the first Bacillus species or modified such that it functions equivalently to the expression element per se, or may be a synthetically created sequence which functions equivalently.

In the context of this invention, "isolated" means that the expression element is separated from its naturally occurring environment.

The source of DNA from which to isolate the fragment containing the SacB[BamP] gene can be, for example, any *Bacillus amyloliquefaciens.* These bacteria are available from the American Type Culture Collection, 12301 Parklawn Drive, Rockville, MD 20852. A non-limiting example of one such culture is ATCC Accession No. 23844. Cultures of *B. amyloliquefaciens* may be grown by methods well known to bacteriologists. Bacterial DNA, e.g., from *B. amyloliquefaciens,* suitable for cloning to make a library may be obtained conventionally, e.g., as described below. Conventional means can also be used to produce such a library, for example, purchasing and following the manufacturer's instructions for commercially available kits such as λ-ZAP DNA and Giga pack plus (Stratagene, 11099 North Torrey Pines Road, La Jolla, CA 92037).

To pick the clone of DNA containing the levansucrase gene, an oligonucleotide probe can be made consisting of more than 13 bases and whose sequence of bases is selected from the sequence of bases encoding levansucrase in *B. subtilis* [Steinmetz et al., Mol. Gen. Genet 200:220-228 (1985)] or the sequence of bases encoding levansucrase in *B. amyloliquefaciens* (see FIG. 3). Such probes can be synthesized by standard methods, or they may be purchased commercially. Two examples of probes that can be used are those with the following sequences:

GACGTTTGGGACAGCTGGCCAT-TACAAAAC and

ATGAACGGCAAATGGTACCTGTTCACT-GAC.

It is important that the fragment isolated contain at least the 893 nucleotide pairs in the 3' direction from the 5' end that starts with an Eco RI restriction endonuclease site, as the nucleotides contained therein constitute the expression elements and the sequence for the signal peptide of the levansucrase gene.

To obtain the desired sequence, it is convenient to isolate a larger fragment containing not only the expression elements, but also the sequences encoding the signal peptide, the mature levansucrase gene, and possibly a few base pairs from the cloning vector. This can be accomplished by converting the phage clones, identified and purified from the library by means of specific probes and standard microbiological selection methods, to a Blue Script plasmid vector (Stratagene, supra) according to the manufacturer's instructions. A DNA fragment comprising the desired expression elements and the sequences encoding the signal peptide and the mature levansucrase can be isolated from the Blue Script plasmid by digesting it with EcoRV and XbaI and isolating and recovering a fragment containing at least 2350 nucleotide base pairs. The resulting fragment can be inserted into any vector that can exist as a multicopy plasmid in gram-positive bacteria and represents one aspect of this invention.

One preferred aspect of this invention is a vector constructed by further modifying the 2350 base pair fragment by inserting one or more restriction endonuclease cleavage sites at the 3' end of the first 893 base pairs (i.e., at the 3' end of the 29 base pair signal sequence) near the start codon for the mature levansucrase. One such restriction endonuclease site is that of EcoRV; it can be inserted by site-directed mutagenesis by following the directions accompanying a commercially available mutagenesis kit, for example, the Mutagene phagemid in vitro mutagenesis kit from BioRad, 1414 Harbour Way South, Richmond, CA 94894 (Smith [1985], supra). The inserted restriction endonuclease cleavage site or sites offers a convenient way to insert the genetic information encoding foreign proteins of interest to bring the expression of that genetic information under the control of the preceding expression elements. A vector of the preferred type is then made by inserting the modified fragment comprising the expression, regulatory, and signal sequences from a Bacillus species, preferably *B. amyloliquefaciens,* into a plasmid vector that can exist as a multicopy plasmid in gram positive bacteria. Gram positive bacteria, especially *B. subtilis,* transformed with a vector of this invention (i.e., the preferred 2350 base pair fragment modified to contain a restriction endonuclease cleavage site just downstream of the signal sequence and a DNA sequence coding for a polypeptide attached thereto in the proper reading frame), when and only when in the presence of sucrose, produce and secrete into the medium whatever protein is encoded by the genetic sequence operably linked to the modified fragment by means of the inserted restriction endonuclease site or sites.

It is to be noted that, although conventional techniques for selecting suitable clones containing the sacB-[BamP] gene from the *B. amyloliquefaciens* library can be used, e.g., making synthetic probes based on the expected homology of *B. amyloliquefaciens* with the known sequence of the *B. subtilis* levansucrase gene, there is still a sufficient heterogeneity between the genes from the two species to prevent deleterious recombination events from occurring between the chromosomal gene of the host cells and the heterologous gene engineered according to this invention and encoded on a multicopy plasmid. Thus plasmid instability may be avoided by the use of the vector of this invention.

In view of the information contained in this disclosure, a set of probes can be designed, for example, 2-4 probes, which correspond to regions of the levansucrase gene and its expression elements which are homologous substantially throughout Bacillus species. Using standard techniques for genetic engineering, one can routinely screen a library constructed from any *Bacillus* species to routinely pick out the desired gene homologous to that of this invention, or other expression element and signal peptide DNA sequences that are similarly homologous. Other likely Bacillus species which may be used as the source of the expression system include *B. pumilis, B. brevis, B. licheniformis,* and *B. stearothermophilus.* Moreover, by determining highly conserved regions of the gene in Bacillus, corresponding probes can be designed routinely to pick out levansucrase genes of related genera.

Thus it can be seen that, using the vectors and methods of this invention, it is now possible to transform a wide variety of bacterial hosts with a stable vector of this invention in order to express a heterologous polypeptide therein. It is further possible, if the host species contains regulatory elements compatible with those of the expression element on the vector, to regulate such expression. It is further possible, using techniques known to one of skill in the art, to additionally co-transform those regulatory elements which may be needed for regulated expression of a vector of this invention into a species lacking these regulatory elements, such that a vector of this invention may be expressed in a regulated fashion in a species not normally containing these regulatory elements, if desired. Thus a preferred aspect of this invention provides vectors, bacterial strains and methods for producing heterologous polypeptides in Bacillus strains in a regulated fashion, either intracellularly or secreted into the culture medium. Another preferred aspect of this invention is to provide vectors, bacterial strains and methods for producing heterologous polypeptides in non-Bacillus, preferably, but not necessarily, gram positive bacteria, in a non-regulated fashion, either intracellularly or secreted into the culture medium.

Without further elaboration, it is believed that one skilled in the art can, using the preceding description, utilize the present invention to its fullest extent. The following preferred specific embodiments are, therefore, to be construed as merely illustrative and in no way limitative of the remainder of the disclosure.

In the foregoing and in the following examples, all temperatures are set forth uncorrected in degrees Celsius; and, unless otherwise indicated, all parts and percentages are by weight.

The entire texts of all applications, patents and publications cited herein are hereby incorporated by reference.

EXAMPLES

A Method for Isolating *B. amyloliquefaciens* DNA

*B. amyloliquefaciens* (25 ml) is grown for 5 hours in Penassay medium (Difco, Detroit, Michigan). The bacteria are collected by centrifugation and resuspended in 5 ml of 50 mM Tris-50 mM EDTA buffer (pH 8.0). Lysozyme is added to a final concentration of 800 μg per ml, and the resulting mixture is incubated at 37° C. for 15 minutes. Sodium dodecyl sulfate and Proteinase K (final concentrations of 0.5% and 50 μg per ml, respectively) are added, and the resulting mixture is incubated for 5 minutes. The sample is then mixed with an equal volume of Tris buffer (100 mM, pH 8.0) saturated phenol. After removal of the phenol, the aqueous layer is extracted twice with equal volumes of chloroform isoamyl alcohol (24:1). The resulting aqueous layer is removed, and NaCl is added to a final concentration of 0.4 M. Two volumes of ethanol are added gently, and the DNA is swirled and removed from the interphase with a Pasteur pipette. The isolated DNA is rinsed in a 70% ethanol solution and dried in vacuo. The isolated DNA is solubilized in 10 mM Tris-1 mM EDTA and its concentration determined using methods well known to those skilled in the art.

EXAMPLE 1

Isolation of the sacB[BamP] Gene

The sacB[BamP] gene of *B. amyloliquefaciens,* which codes for levansucrase (lvs), was isolated from a λ ZAP library of the *B. amyloliquefaciens* chromosome using oligonucleotide probes as a means of identifying clones containing the appropriate sequences. The *B. amyloliquefaciens* λ library was constructed using the commercially available EcoRI-digested λ-ZAP DNA and Giga pack plus (Stratagene, 1109 North Torrey Pines Road, La Jolla, CA 92037) according to manufacturer's instructions.

A. Synthesis of Oligonucleotide Probes

Two oligonucleotide probes of 30 bases each were synthesized, their sequences being based on the reported nucleotide sequence for the *B. subtilis* (sacB[-Bsu1) gene (Steinmetz et al., supra). The sequence of each oligonucleotide probe is set forth below:

| Probe No. | Nucleotide Sequence |
|---|---|
| 52142-2NP | GACGTTGGGACAGCTGGCCATTACAAAAC |
| 52142-3NP | ATGAACGGCAAATGGTACCTGTTCACTGAC |

A one μl (400 ng) sample of each probe was 5' end labeled with =P λ ATP, as described in the standard protocol (Maniatis et al., ibid., p. 122). Equal amounts of the two probes (52142-2NP and 52142-3NP) were pooled and mixed for further use.

B. Infection of Host Cells and Screening of the *B. amyloliquefaciens* Library The procedures used were essentially those described in Maniatis et al., suora. *E. coli* strain BB4 were used as host cells and infected with 5 μ of the *B. amyloliquefaciens* λ ZAP phage plaques/plate. The infected cells were plated to a concentration of 1000–1500 on 8 NZYM plates by the pour plate method using 3.0 ml of NZYM top agar. Plates were incubated at 37° C. overnight. The DNA from the resulting plaques was transferred to nitrocellulose filters. The filters were then screened for the presence of the *B. amyloiquefaciens* sacB[BamP] gene using the radio-labeled oligonucleotide probes shown above (52142-NP and 52142-3NP). A total of 11,200 plaques were screened.

The labeled oligonucleotide probes (52142-2NP and 52142-NP) (60 ng) were hybridized to the nitrocellulose filters in 6×SSC/0.5% SDS buffer at 37° C. for 16 hours. The nitrocellulose filters were washed in 6×SSC/0.1% SDS buffer. The first wash was at room temperature and the second at 37° C. Subsequent autoradiographs of the filters revealed 5 clones which hybridized with the probes. However, because there was high background activity, the filters were again washed at 37° C. The resulting autoradiographs of the filters indicated that there were two clones (designated 2A and 2C) potentially containing DNA which hybridized to the probes.

C. Isolation and Purification of Phage Plaques Containing the sacB[BamP] Fragment Plaques which hybridized with the probes were isolated and phage therein purified according to the Maniatis et al., supra. The infection and screening procedures were repeated (secondary screen). In the secondary screen, about 20% and 80% of plaques from phage clones 2A and 2C, respectively, hybridized with the probes. Positive plaques from these secondary screens were then selected, phages prepared, and further screened. Autoradiographs from the tertiary screens showed that all the plaques hybridized the oligonucleotide probes. Both clones 2A and 2C were screened.

D. Isolation of λ DNA and Excision of Phagemid (Blue Script)

λ ZAP phage clones 2A and 2C containing the putative sacB[BamP] gene sequences were converted to Blue Script plasmid vectors by following the manufacturer's (Stratagene) instructions. The resulting Blue Script plasmids from λ ZAP 2A clones and λ ZAP 2C clones were designated pBE300 and pBE301, respectively.

E. Characterization of the Cloned *B. amyloliquefaciens* DNA Fragment

Plasmid DNA was isolated separately from pBE300 and pBE301 plasmids according to Stratagene's instructions. The DNA (5 μl) from each plasmid was digested with EcoRI in 20 μl total volume. The resulting restriction fragments were analyzed by polyacrylamide gel electrophoresis (PAGE) through a 0.8% gel, as described in Maniatis et al., ibid., p. 64. The EcoRI digest of pBE 300 yielded 2 bands corresponding to fragments 3.0 and 1.5 kb in size, while the EcoRI digest of pBE301 yielded bands corresponding to DNA fragments with sizes of 3.0 and 1.5, as did digests from pBE300, and an additional 0.6 kb fragment. The radiolabeled oligonucleotide probes (52142-2NP and 52142-3NP) were hybridized to the fragments according to the Southern hybridization method described in Maniatis et al., ibid. The probes hybridized only with the 1.5 kb fragment, suggesting that it contained the sacB[BamP1 gene. Restriction mapping demonstrated that the 0.6 kb fragment was oriented 5' to the 1.5 kb fragment. The 3.0 kb fragment corresponds to the size of the Blue script vector (2.9 kb). A detailed restriction map of pBE301 is shown in FIG. 1.

Figure 2:
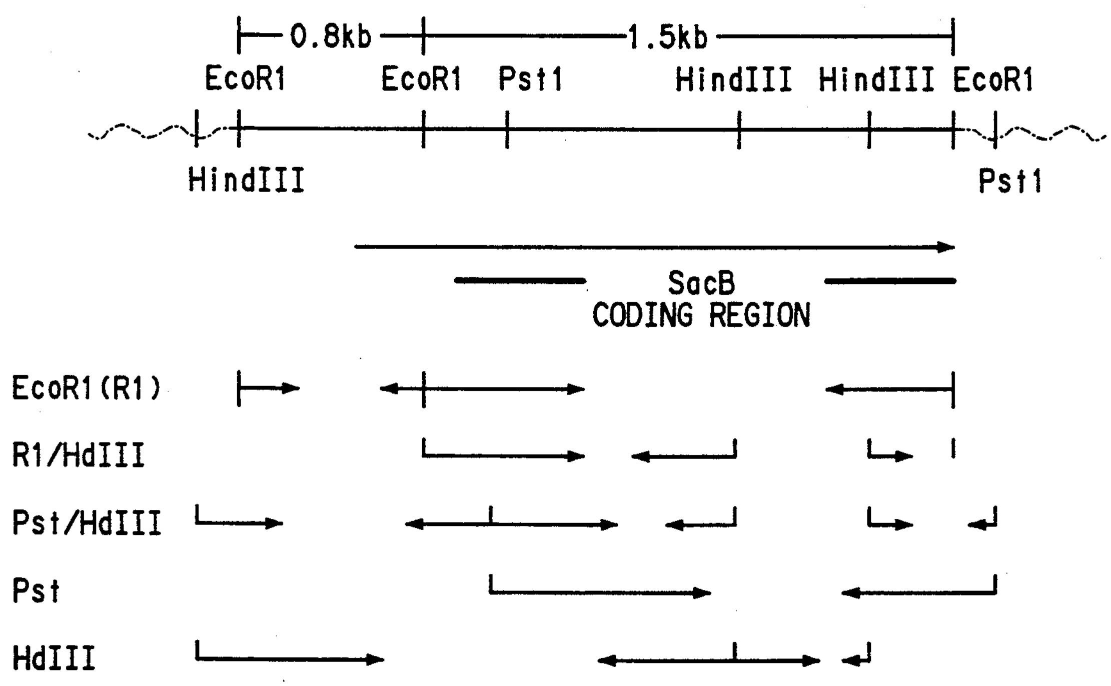
FIG. 2: Restriction map and sequencing strategy for sequencing the isolated sacB[BamP] fragment. The arrows indicate the sequence that was generated in each of several clones.
Figure 3B:
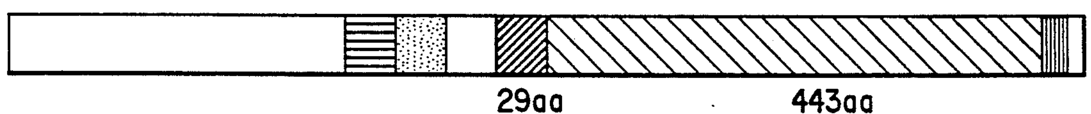
FIG. 3*b*: Schematic representation of the sacB[BamP] sequence.

The sequencing strategy for both EcoRI fragments is outlined in FIG. 2. Various restriction fragments were cloned into phage vectors M13mp18 and M13mp19 (purchased from Pharmacia, Inc., 800 Centennial Avenue, Piscataway, NJ 08854). DNA sequences were obtained by using a Sequenase TM sequencing kit purchased from United States Biochemical Corp., P.0. Box 22400, Cleveland, Ohio. Several overlapping clones of both strands were sequenced, and the data revealed that the 0.6 kb and 1.5 kb fragments were, respectively, 801 bp and 1,549 bp in length. Thus, a contiguous 2,350 base nucleotide sequence was generated (see FIG. 3*a*). An analysis of the sequence showed a large open reading frame encoding 472 amino acids. There were two potential initiation codons at −31 and −29 preceding the mature protein. However, only codon −29 was preceded by a Bacillus ribosome binding site [McLaughlin et al., J. Biol. Chem. 256:11283–11291 (1981)]. Thus, the signal peptide for levansucrase is probably 29 amino acids in length, and the mature protein contains 443 amino acids. An analysis of the DNA sequence upstream from the coding region reveals a regulatory sequence (bp 706 to pb 764), preceded by DNA sequences that resembled a promoter sequence that seems to be recognized by the major form of *B. subtilis* RNA polymerase (SigA) [Losick et al., Ann. Rev. Gen. 20:625–669 (1986)]. The end of the coding region has an inverted repeat which resembles a rho-independent transcriptional terminator. A schematic representation of this analysis is shown in FIG. 3*b*.

The nucleotide sequences of sacB[BamP] and sacB[-Bsu] were compared using the Wisconsin data base Gap program. A homology of 82.6% was observed. The deduced amino acid sequence of the mature proteins show 90% homology.

The free energies of the stem and loop structures in the putative regulatory regions of sacB[BamP] were compared with the data of Shimotsu et al. (supra) for the *B. subtilis* sacB gene and its two constitutive regulatory mutants to see whether any correlation can be found between the regulation and the free energy (the higher the free energy, the better the regulation). The free energy calculations did nct reveal whether one could predict that sacB[BamP1 would be regulated by sucrose in *B. subtilis*.

EXAMPLE 2

Regulatable Expression of *B. amyloliquefaciens* levansucrase in *B. subtilis*

Figure 5:
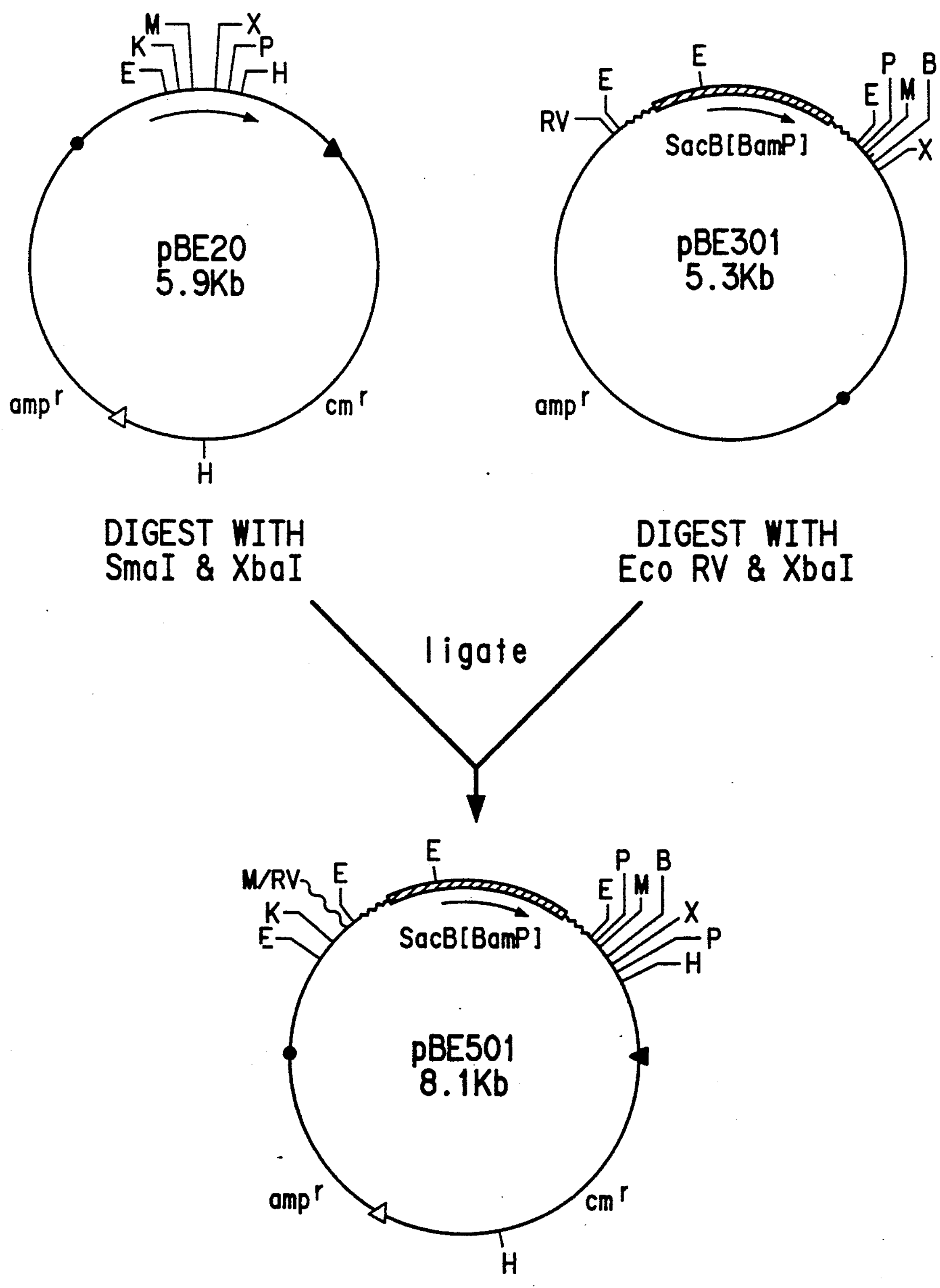
FIG. 5: Construction of the sacB[BamP1 shuttle vector pBE501. The symbol o denotes the pBR322 ori, the symbol ▲ denotes pC194 ori, and the symbol Δ denotes fl ori.

The EcoRV-XbaI fragment of sacB[BamP] from pBE301 was cloned into plasmid pBE20, as outlined in FIG. 5, resulting in new vector pBE501. pBE20 is an *E. coli-B. subtilis* shuttle vector containing an Fl origin. pBE20 was constructed by ligating HindIII digested pTZ18R (Pharmacia), which contains an origin of replication for *E. coli*, an Fl ori and antibiotic resistance marker ampR, with HindIII digested pC194 (Bacillus Stock Center, Ohio State University, Columbus, OH 43210), a *Staphylococcus aureus* plasmid which is a multicopy plasmid in *B. subtilis* and which contains a chloramphenicol resistance marker for selection in *B. subtilis*. pBE501 is also an *E. coli-B. subtilis* shuttle vector, and *B. subtilis* strain BE1010 was transformed with pBE501 and pBE20. Levansucrase levels were determined for cultures of bacteria transformed with each of the plasmids, each transformed culture being grown in Penassay medium containing 50 μl $MnCl_2$ for 8 hours, in the presence and absence of 2% sucrose. Cells were separated from the supernatant, and protease inhibitor (phenyl methyl sulfonyl fluoride) was added (1 mM final concentration). The pH of the supernatant was adjusted to pH 4.2 by adding acetic acid and an equal volume of ethanol and mixing thoroughly. After incubating at 4° C. overnight, precipitated protein was collected by centrifugation at 39,000 Xg for 30 minutes. The protein was solubilized in 50 mM potassium phosphate buffer, pH 6.0. Levansucrase activity was measured by determining the amount of glucose released from sucrose. The enzyme was assayed at 37° C. for 30 minutes by incubating it in a solution of 50mM potassium phosphate buffer (pH 6.0) containing 1% sucrose. The enzyme was inactivated by heating at 70° C. and the amount of glucose determined by using the Glucose Trinder TM Kit from Sigma (Sigma Chemicals, P.0. Box 14508, St. Louis, MO 63178, Cat. No. 315-100). The activity is expressed as the amount of glucose released per ml of the culture per hour at 37° C. One unit corresponds to 1 μg of glucose released per hour per ml of the culture supernatant.

As shown in Table 1, levansucrase activity was detected only when the strains were grown in the presence of sucrose. The activity observed in the bacterial culture transformed with pBE20 is due to the expression of sacB[Bsu] normally present in *B. subtilis*.

TABLE 1

| | +sucrose | −sucrose |
|---|---|---|
| pBE20 (vector) | 58.2* | 4.7 |
| pBE501 (sacB[Bamp]) | 287.0 | 2.2 |

*this represents the units of activity due to chromosomal sacB[Bsu]
(A *B. subtilis* strain I5194 with a mutation in the chromosomal sacB[Bsu] was also transformed with pBE20 and pBE501. Levansucrase activity was detected only in the presence of sucrose and only in the cultures of bacteria transformed with pBE501.)

EXAMPLE 3

Demonstration of the Regulatable Functionality of the Cloned Expression Elements of the Levansucrase Gene of *B. amyloliquefaciens*

The promoter cloning vector pPL703, as described by Williams et al., J. Bacteriol. 146:1162–1165 (1981) (Bacillus stock center), which contains the promoterless cat86 gene (chloramphenicol resistance) was used to additionally evaluate the sucrose inducible nature of the sacB[BamP] promoter/regulatory region. The 0.8 kb EcoRI fragment of pBE301 was cloned at the EcoRI site of pPL703, resulting in pBE305. *B. subtilis* BR151 was transformed with pBE305 and plated on tryptose blood agar base plates [TBAB agar (Difco, Detroit, Michigan)+Kan (20 μg ml)]. Colonies were picked and patched onto agar plates containing TBAB+cm (10 μg/ml), as well as on agar plates containing TBAB+2% sucrose+cm (10 μg/ml). Chloramphenicol resistance was only observed on those plates which contained sucrose. *B. subtilis* transformed with pPL703 alone did not have detectable CAT activity, irrespective of the presence of sucrose. Thus, the sacB[BamP] promoter can be regulated by sucrose on a multicopy plasmid and used for intracellular protein expression in *B. subtilis.*

EXAMPLE 4

Constructioon of a Regulatable sacB[BamP]-based Secretion Vector with a Restriction Endonuclease Cleavage Site Secretion vectors in *B. subtilis* must provide the following expression elements: transcriptional and translational start sites and a signal peptide coding region. In order to easily construct heterologous gene fusions, an EcoRV site was created in sacB[BamP] two codons downstream from the 3' end of the signal peptide coding region, as shown in FIG. 6. Site-directed mutagenesis was performed using a Muta-gene phagemid in vitro mutagenesis kit from BioRad, 1414 Harbour Way South, Richmond, CA 94804. Single-stranded template from pBE504 (pBE504 is similar to pBE501, except it contains two additional silent mutations in the signal peptide) was prepared, and an oligonucleotide (CTTCGCGAAAGAAGATATCAATAAC-CAAAAAGC) was used to create the EcoRV site by a six base insertion. The presence of the EcoRV site was determined by restriction digestion and later confirmed by DNA sequencing. The resulting plasmid is designated pBE311 (see FIG. 6). *B. subtilis,* strain BE1010 was transformed with pBE311, and levansucrase activity was measured in the culture supernatant showing that the introduction of the two amino acids (aspartic acid and isoleucine) coded for by the six base insertion did not affect the enzyme activity.

EXAMPLE 5

The Regulatable Secretion of a Foreign Gene Product

Figure 7:
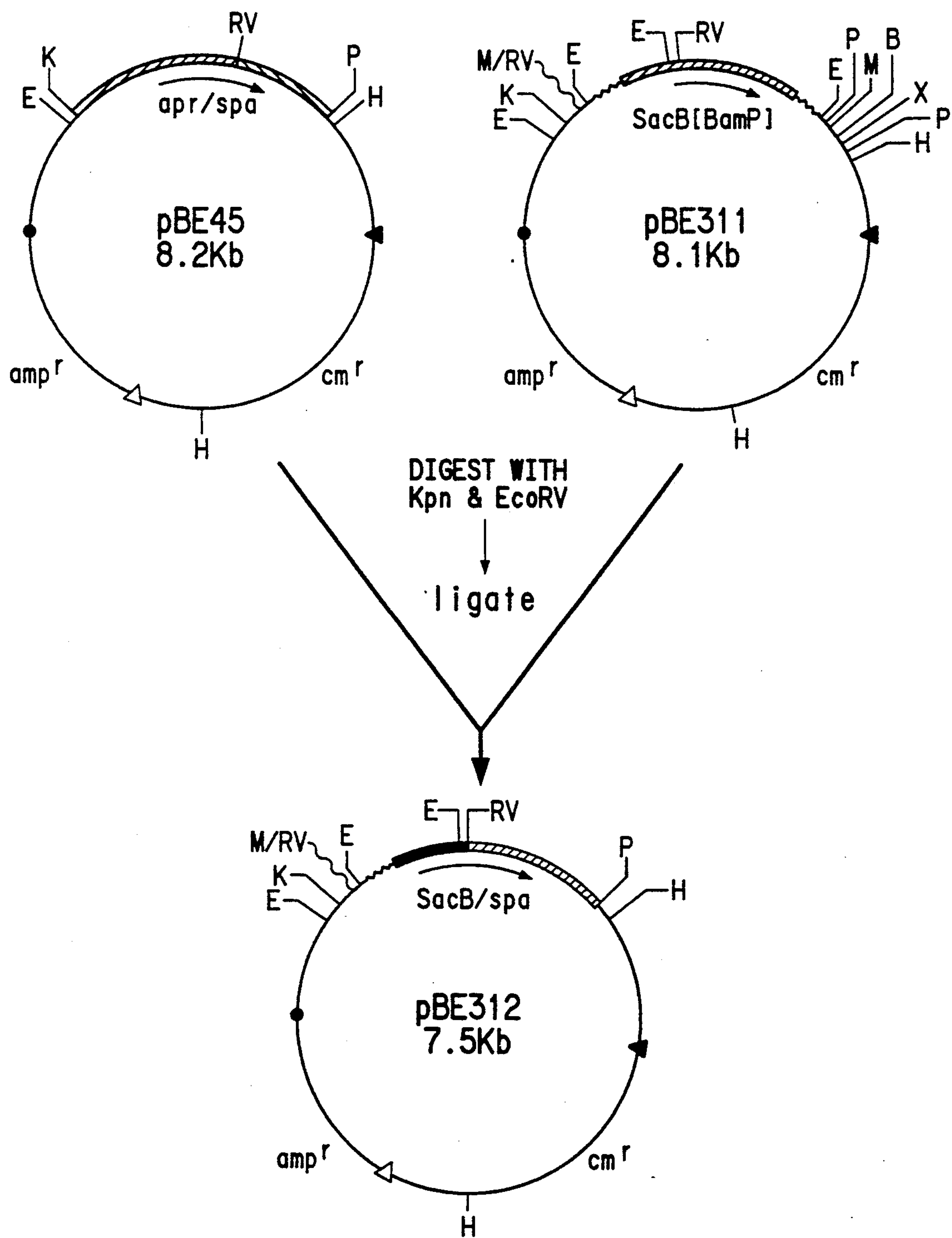
FIG. 7: Construction of pBE312.

An example of a heterologous gene whose product can be regulatably produced by inserting the gene into the preferred vector of this invention was that for staphylococcal protein a (soa). The soa gene was obtained from plasmid pRIT5, which was purchased from Pharmacia, 800 Centennial Avenue, Piscataway, NJ 08854. The spa gene from pRIT5 does not contain any convenient restriction site which can be fused to the EcoRV site of pBE311. Neither was it known a priori whether or not protein A would be secreted when fused to sacB-[BamP]. However, it had been demonstrated (Vasantha, N. and Thompson, L. D., J. Bacteriol. 165, 837–842 [1986]) that the *B. amyloliquefaciens* alkaline protease signal peptide can traslocate protein A. pBE26, which is a pBE20-based vector, contains the alkaline protease gene (apr) from *B. amyloliquefaciens* (Vasantha, ibid.) and a unique EcoRV site two codons downstream from the alkaline protease signal peptide coding region. pBE26 was digested with EcoRV and Pst and ligated to pRIT5, which had been digested with Bcll. The 5' overhang was filled in to generate a blunt end compatible with EcoRV. The resultant plasmid was then cut with Pstl. The correct plasmid was designated pBE35 and had lost both the Bcll site and the EcoRV site. An EcoRV site was recreated by site-directed mutagenesis at the Bcll-EcoRV junction. The resulting plasmid was designated pBE45. Thus, pBE45 contains an aor-soa fusion where the Bcll site in the mature protein A sequence was converted to an EcoRV site by the site-directed mutagenesis. pBE45 and pBE311 were digested with Kpn-EcoRV and ligated. The plasmid with the correct restriction pattern was selected and designated pBE312 (see FIG. 7), and the DNA sequence across the fusion junction showed that the correct sacB-[BamP]-spa sequence had been obtained.

Cultures of *B. subtilis* strain BE1010 (ΔaprE, Δnpr, $trpC_2$, metB10, lys3) were separately transformed with pBE312 or pBE20 and plated on TBAB+2% sucrose+Cm (5 μg/ml), overlayered with nitrocellulose and cellulose acetate filters. The plates were incubated overnight. The nitrocellulose filter was then removed and processed by colony immunoassay [Saunders et al., J. Bacteriol. 169:2917–2925 (1987)]. Colonies with Protein A positive phenotypes were observed only when sucrose had been present in the bacterial medium. Additionally, cultures of *B. subtilis* strain BE1010 transformed with pBE312 were grown in the presence and absence of sucrose. Both the cellular and the culture supernatant fractions were analyzed for Protein A by immunoblotting. Protein A was found primarily (>95%) in the culture supernatant of those cultures incubated with sucrose, and only minor amounts (<5%) associated with the cellular material. The cultures incubated in the absence of sucrose were found to have only very low levels of Protein A, due to very slight constitutive readthrough of the expression vector.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications to the invention to adapt it to various usages and conditions.

What is claimed is:

1. A sucrose regulatable recombinant expression vector capable of transforming a host *Bacillus subtilis,* comprising:
   a) a sucrose-regulatable expression element derived from the *Bacillus amyloliquefaciens* levansucrase gene which comprises a promoter sequence and a regulatory sequence which is regulatable by sucrose or a sucrose analog; and
   b) a DNA sequence operably linked to the expression element and enclosing a polpeptide.

2. A vector of claim 1 wherein the polypeptide is levansucrase.

3. A vector of claim 1, wherein the polypeptide is hetrologous to the expression element.

4. A vector of claim 1, wherein the sucrose analog is thiosucrose.

5. A vector of claim 1, wherein the vector is a plasmid.

6. A vector of claim 1, further comprising a DNa sequence coding for a signal peptide.

7. A vector of claim 6, wherein the DNA coding for the signal peptide is derived from a levansucrase gene.

8. A vector of claim 6, wherein the DNA coding for the signal peptide is derived from a gene heterologous to the expression element.

9. A vector of claim 1, further comprising a unique restriction endonuclease cleavage site downstream of the expression element.

10. A vector of claim 6, further comprising a unique restriction endonuclease cleavage site downstream of and operably linked to the DNA sequence coding for the signal peptide.

11. A *Bacillus substilis* transformed with the sucrose or sucrose analogue regulatable expression vector of claim 1.

12. A *Bacillus subtilis* of claim 11, wherein said vector further comprises DNA coding for a signal peptide.

13. A *Bacillus subtilis* of claim 12, wherein the signal peptide is derived from a levansucrase gene from *Bacillus amyloliquefaciens.*

14. A method of regulatably producing a polypeptide encoded by a hetrologous gene in *Bacillus subtilis,* comprising:

a) growing the transformed *Bacillus subtilis* of claim 11 in an appropriate nutrient medium under conditions whereby the heterologous gene is expressed; and b) isolating the polypeptide.

15. A method of regulatably producing a polypeptide encoded by a heterologousgene in *Bacillus subtillis,* comprising:

a) growing the transformed *Bacillus subtilis* of claim 12 in an appropriate nutrient medium under conditions whereby the heterologous gene is expressed; and b) isolating the polypeptide.

16. A method of claim 14, wherein the polypeptide is levansucrase.

17. A vector according to claim 1, selected from the group consisting of pBE300, pBE301, pBE501, pBE305, pBE504, pBE311, pBE312.

18. A DNA fragment, comprsing:

a) a sucrose-regulatable expression element derived from the *Bacillus amyloliquefaciens* levansucrase gene, said expression element comprises:

i) a promoter sequence, and ii) a regulatory sequence which is regulatable by sucrose or a sucrose analog; and said expression element being operably linked to;

b) a DNA sequence encoding a polypeptide, wherein the DNA fragment is expressible under sucrose regulation in a host *Bacillus subtilis.*

* * * * *